United States Patent
Tyler

(10) Patent No.: US 6,244,269 B1
(45) Date of Patent: Jun. 12, 2001

(54) GUM JOB

(76) Inventor: John Tyler, 2010 Helen St., Melbourne, FL (US) 32901

( * ) Notice: Subject to any disclaimer, the term of this patent is extended or adjusted under 35 U.S.C. 154(b) by 0 days.

(21) Appl. No.: 09/300,569

(22) Filed: Apr. 27, 1999

(51) Int. Cl.[7] .................................................. A61C 5/14
(52) U.S. Cl. .......................................... 128/859; 128/861
(58) Field of Search .................................. 128/846, 848, 128/859–862; 602/902

(56) References Cited

U.S. PATENT DOCUMENTS

| | | |
|---|---|---|
| 1,986,988 | 1/1935 | Treadwell . |
| 3,126,002 * | 3/1964 | Owens ................................. 128/861 |
| 4,338,928 | 7/1982 | Martin et al. ......................... 128/136 |
| 4,600,387 | 7/1986 | Ross ..................................... 433/136 |
| 4,947,731 | 8/1990 | Harding ............................... 128/842 |
| 5,016,649 | 5/1991 | Johnson ............................... 128/859 |
| 5,176,151 | 1/1993 | Harding ............................... 128/842 |
| 5,328,711 | 7/1994 | Coleman et al. ..................... 426/576 |
| 5,409,016 | 4/1995 | Bloodsaw ............................. 128/842 |
| 5,427,117 * | 6/1995 | Thornton ............................. 128/861 |
| 5,499,633 | 3/1996 | Fenton ................................. 128/848 |
| 5,582,187 | 12/1996 | Hussey ................................. 128/857 |
| 5,970,981 * | 10/1999 | Ochel ................................... 128/859 |

* cited by examiner

Primary Examiner—Michael A. Brown
(74) Attorney, Agent, or Firm—Brian S. Steinberger; Law Offices of Brian S. Steinberger

(57) ABSTRACT

A two piece pliable, edible, flavored mouthpiece to be worn by one consenting adult performing oral sexual activities such as cunnilingus and fellatio, and the like, on another consenting adult. The mouthpiece can be formed from pliable flavored edible materials such as but not limited to starch jellied candies, gelatin candy(i.e. Gummy Bears TM), starch gelatin, licorice, chewing gum, and the like. The mouth piece includes a top U-shaped single piece set for fitting about the front top and partial top side teeth of the wearer, and a bottom U-shaped single piece set for fitting about the front bottom and partial bottom side teeth of the wearer. The wearer clenching down customizes the fit of the mouthpiece therein and changes the sharp hard edges of the teeth to be soft and rounded. Each piece uses more material adjacent to between the front teeth, tapering to less material toward the back of the side teeth. Optionally, at least one of the top and bottom teeth members can have a half circular through hole, through a center portion of the front teeth section to allow a portion of another person's body part such as a tip portion of a person's tongue, nipple, toes, fingers, clitoris, penis, and/or body fluids to pass therethrough.

11 Claims, 5 Drawing Sheets

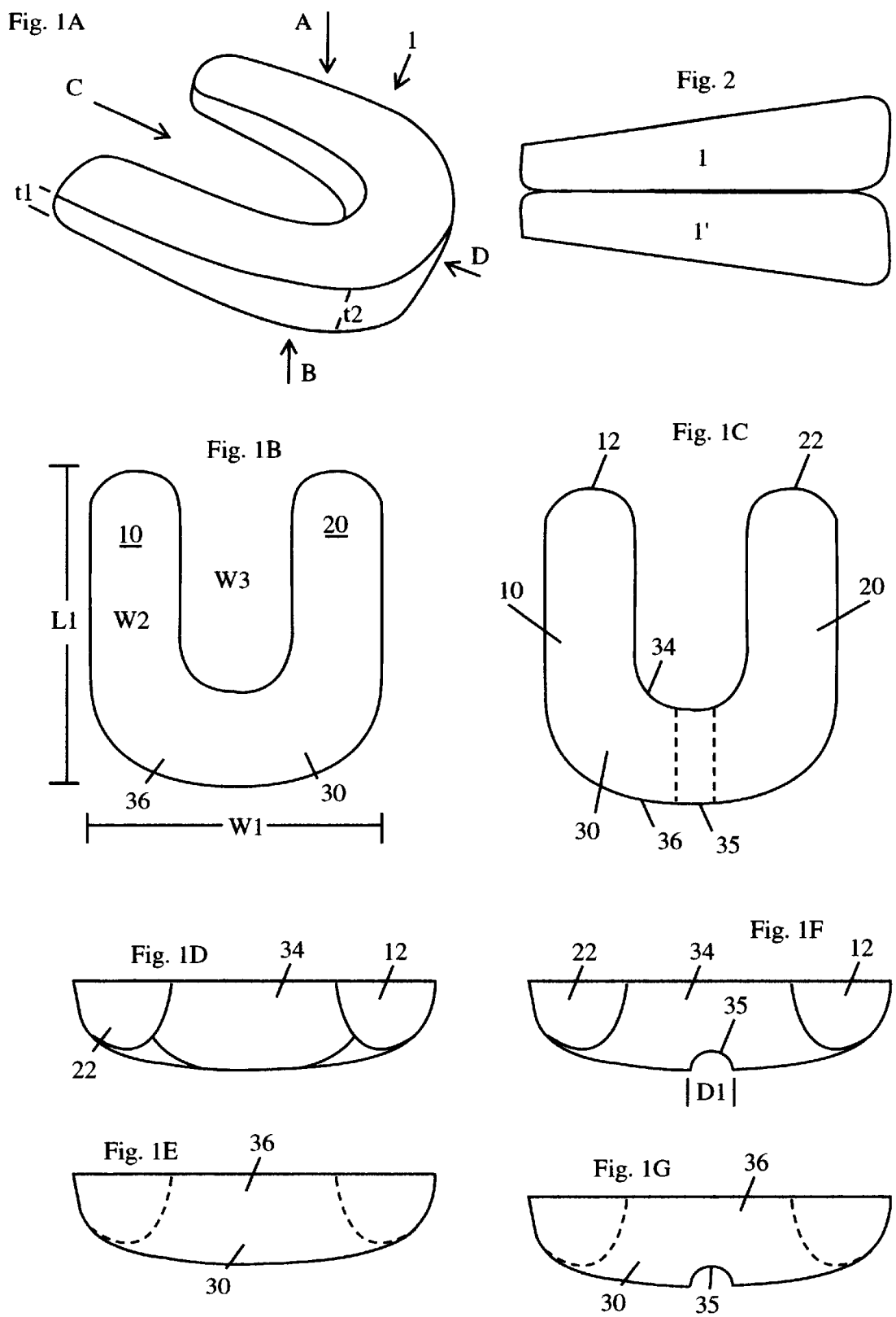

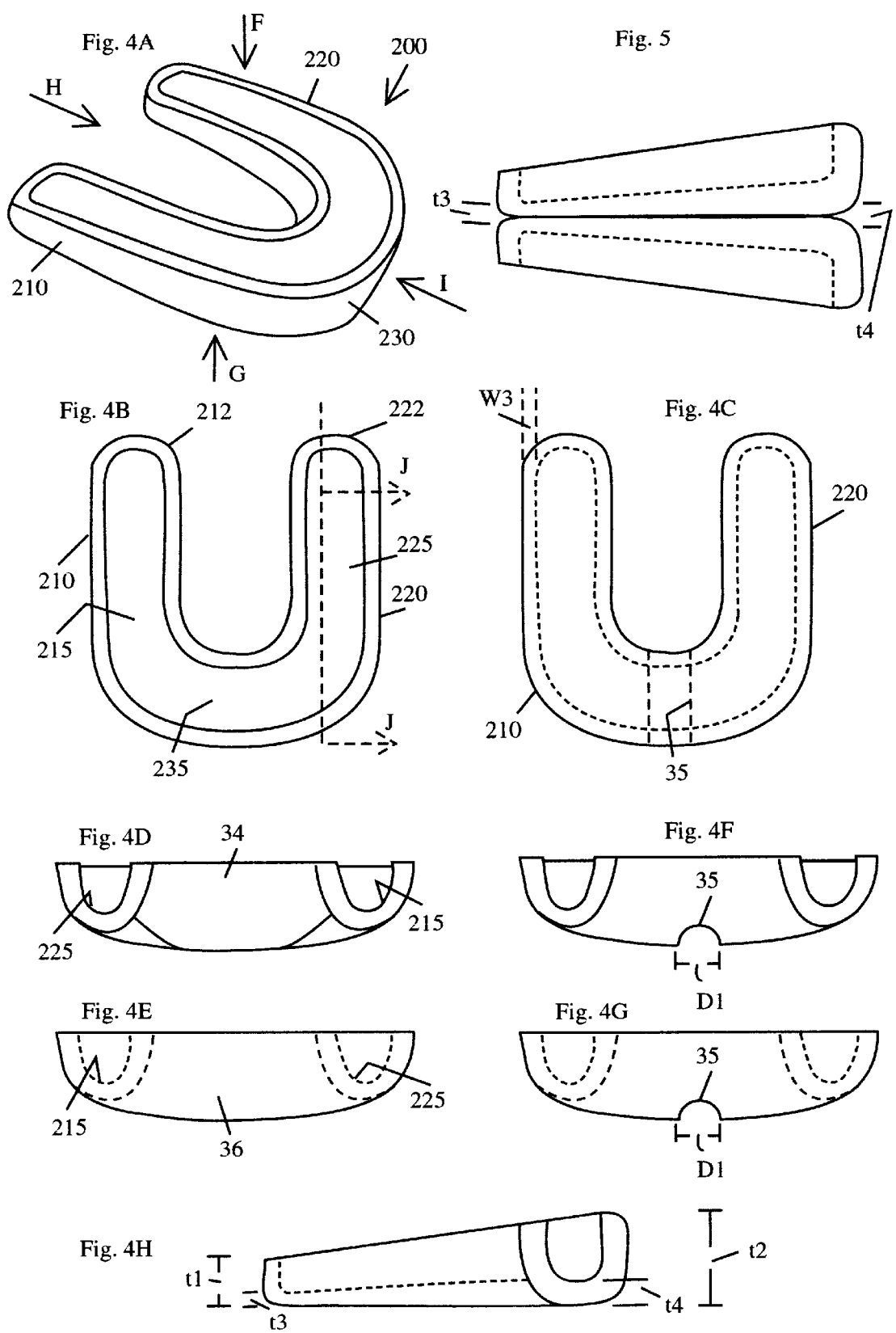

US 6,244,269 B1

GUM JOB

This invention relates to sexual novelty products, and in particular to an edible, pliable mouthpiece worn over the front top and bottom teeth rows of a user performing oral sex.

BACKGROUND AND PRIOR ART

Oral sexual activities between consenting adults such as cunnilingus, fellatio, and the like, require one partner to actively utilize their mouth during the activity. Condoms and oral contraceptives/masks are popular types of devices that are used during these activities. However, the primary purpose of these prophylactic type devices are to prevent the spread of infectious sexually transmitted diseases such as AIDS, Herpes, and the like. See for example, U.S. Pat. Nos. 4,949,731 and 5,176,151 to Harding; U.S. Pat. No. 5,016,649 to Johnson; U.S. Pat. No. 5,409,016 to Bloodsaw and U.S. Pat. No. 5,582,187 to Hussey.

All of these patents require an absolute shield between the consenting adult partners so that no bodily fluid is exchanged from one partner to the other partner. None of these patents allow the partners to be able to directly contact each other partner's body parts and body fluids between partners already knowing the other partner's health condition. All of these patents cover scenarios when there is a risk of passing a sexually transmitted disease. For example, long married partners would not have a desire for these devices when they wish to use an aid that enhances the oral sexual activity by not restricting contact between the partner's body parts and body fluids. Furthermore, these patents are limited to being formed from materials that while flexible are generally plastic in nature, and would not be edible. Furthermore, many of these devices are pre-formed into exact shapes and dimensions, and will not conform to the different sized mouths and various sized teeth of various users. Furthermore, many of these devices while flexible donot provide a cushioned surface, and can be both uncomfortable and harmful to the soft human tissue that the devices contact. While the Harding '731 and '151 patents mention that flavor enhancers can be released in their devices, the Harding patents require the entire oral prophylactics be formed from material such as silicone, and the like, which are not normally dissolvable, nor edible to the person using these devices during oral sexual activities.

SUMMARY OF THE INVENTION

The first objective of the present invention is to provide a mouthpiece that can be worn by a consenting adult performing oral sexual activities that is edible.

The second object of this invention is to provide a mouthpiece that can be worn by a consenting adult performing oral sexual activities that is pliable to conform to the different teeth and mouth sizes of all consenting adult users.

The third object of this invention is to provide a mouthpiece that can be worn by a consenting adult performing oral sexual activities that allows for body parts and body fluids to be in direct physical contact between each of the consenting adults.

The fourth object of this invention is to provide a mouthpiece that can be worn by a consenting adult performing oral sexual activities that changes the sharp and hard edges of their teeth to being soft and rounded.

A preferred embodiment of the Gum Job includes a two piece (double bridge) mouthpiece, wherein the top piece fits firmly in place over the heads of the top row of teeth. And the bottom piece fits firmly over the bottom row of teeth. Both pieces are made of a pliable U-shaped edible material such as but not limited to starch jellied candies, gelatin candy (i.e. Gummy Bears TM), starch gelatin, licorice, and chewing gum. When the teeth are closed and compressed into both pieces, the front of the teeth have a cap layer of approximately ½ inch of material between them, and the back teeth have a cap layer of approximately ¼ inch of material between them. The novel mouthpiece takes the normal sharp edges of the teeth to become soft and smooth. Thus, using the novel mouthpiece reduces the likelihood of damage and discomfort during oral sexual activities. An optional through hole can be included which allows a portion of a body part such as a tip portion of a person's tongue, nipple, toes, fingers, clitoris, penis, and/or body fluids to pass therethrough.

A second embodiment puts hollowed out channels inside each of the U-shaped members, so that the wearer's teeth can fit inside the respective channels.

Further objects and advantages of this invention will be apparent from the following detailed description of a presently preferred embodiment which is illustrated schematically in the accompanying drawings.

BRIEF DESCRIPTION OF THE FIGURES

FIG. 1A is a first embodiment perspective view of a single teeth row member set of the novel mouthpiece.

FIG. 1B is a top view of the single teeth row member set of FIG. 1A along arrow A.

FIG. 1C is a bottom view of the single teeth row member set of FIG. 1A along arrow B.

FIG. 1D is a rear view of the single teeth row member of FIG. 1A along arrow C.

FIG. 1E is a front view of the single teeth row member of FIG. 1A along arrow D.

FIG. 1F is a rear view of the single teeth row member of FIG. 1A along arrow C with semi-circle through-hole.

FIG. 1G is a front view of the single teeth row member of FIG. 1A along arrow D with semi-circle through-hole.

FIG. 2 is a side view of two of the single teeth row member sets of FIG. 1A together for use as both an upper teeth set and as a bottom teeth set.

FIG. 4A a second embodiment perspective view of a single teeth row member set of the novel mouthpiece.

FIG. 4B is a top view of the single teeth row member set of FIG. 4A along arrow F.

FIG. 4C is a bottom view of the single teeth row member set of FIG. 4A along arrow G.

FIG. 4D is a rear view of the single teeth row member of FIG. 4A along arrow H.

FIG. 4E is a front view of the single teeth row member of FIG. 4A along arrow I.

FIG. 4F is a rear view of the single teeth row member of FIG. 4A along arrow H with semi-circle through-hole.

FIG. 4G is a front view of the single teeth row member of FIG. 4A along arrow I with semi-circle through-hole.

FIG. 4H is a side cross-sectional view of a leg of the teeth row member of FIG. 4B along arrow J.

FIG. 5 is a side cross-sectional view of the two single teeth members of the preceding figures in position for being inserted into a wearer's mouth.

DESCRIPTION OF THE PREFERRED EMBODIMENT

Figure 3A:
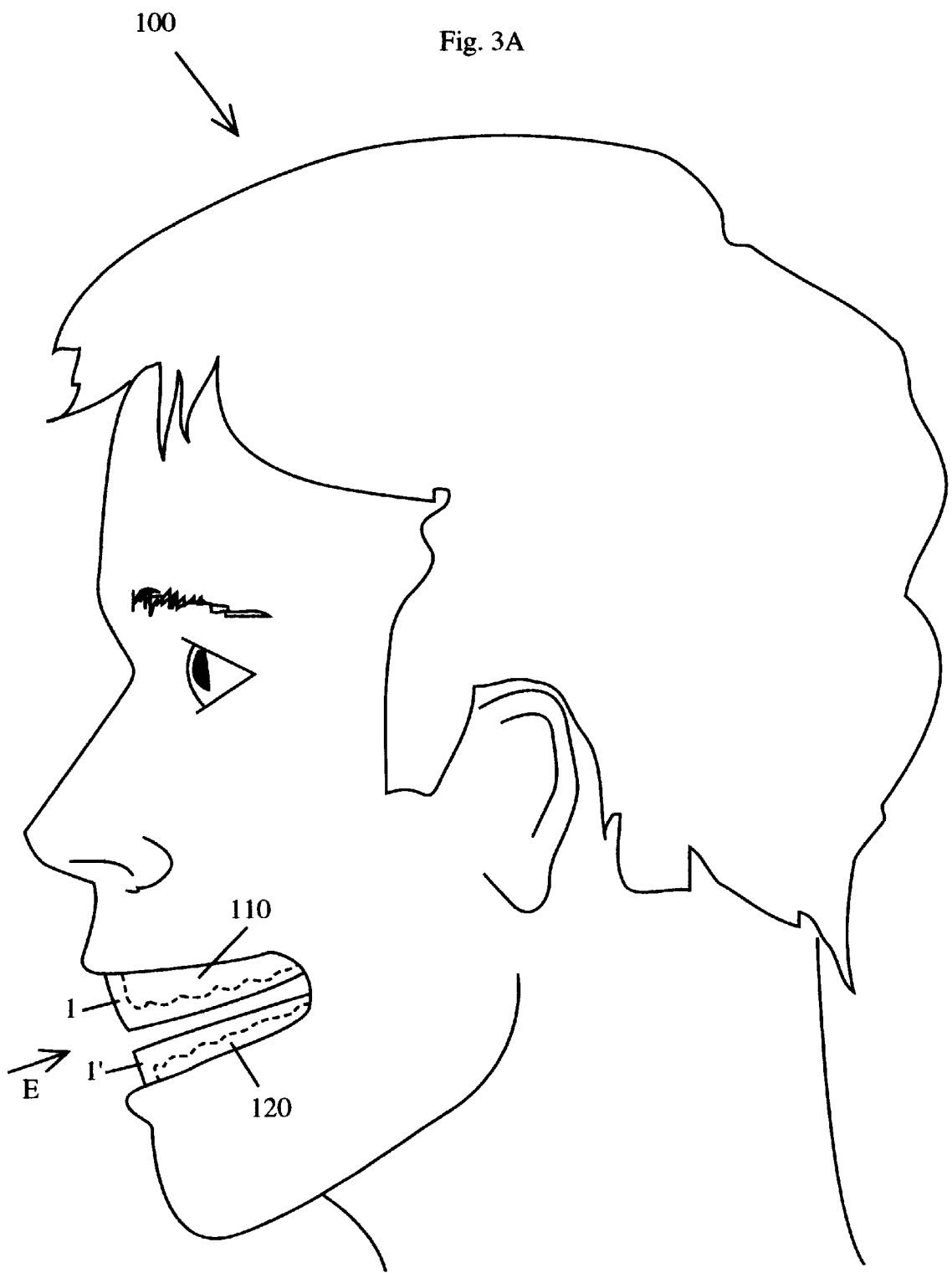
FIG. 3A is a side view of a person wearing two teeth member row sets of FIG. 2 on their teeth.

Before explaining the disclosed embodiment of the present invention in detail it is to be understood that the invention is not limited in its application to the details of the particular arrangement shown since the invention is capable of other embodiments. Also, the terminology used herein is for the purpose of description and not of limitation.

FIG. 1A is a first embodiment perspective view 1 of a single teeth row member set of the novel mouthpiece. FIG. 1B is a top view of the single teeth row member set 1 of FIG. 1A along arrow A. FIG. 1C is a bottom view of the single teeth row member set 1 of FIG. 1A along arrow B. FIG. 1D is a rear view of the single teeth row member 1 of FIG. 1A along arrow C. FIG. 1E is a front view of the single teeth row member 1 of FIG. 1A along arrow D. FIG. 1F is a rear view of the single teeth row member 1 of FIG. 1 A along arrow C with semi-circle through-hole 35. FIG. 1G is a front view of the single teeth row member of FIG. 1A along arrow D with semi-circle through-hole 35.

Referring to FIGS. 1A–1E, each teeth row member set includes a U-shaped configuration having a first leg 10 with rounded end 12, and second leg 20 with rounded end 22, connected together by center piece 30 having an interior facing curved surface 34 and exterior facing curved face 36. Each leg 10, 20 can have a length L1 of approximately 2 to approximately 3 inches long, a thickness t1 at ends 12, 22 having a thickness of approximately ¼ inch that tapers from a bigger thickness t2 of approximately ½ inch at center piece 30.

Referring to FIGS. 1F and 1G, teeth row member 1 can also include semi-circle opening 35 having a diameter of approximately ⅛ inch extending from one side 34 of the center piece 30 to the exterior side 36.

Both top and bottom pieces 1 and 1' can be made of a pliable U-shaped edible flavored material such as but not limited to starch jellied candies, gelatin candy (i.e. Gummy Bears TM), starch gelatin, licorice, chewing gum, chocolate, hard candy, soft and hard candy combinations, and the like. Members can have smooth surfaces, rounded edges, dimpled typed raised areas, combinations thereof, and the like. Additional ingredients can be added to the edible material such as but not limited to edible glow in the dark materials, flavored liquid centers such as those found in Freshen-Up Gum ® and gas releasing materials which cause a fizzle reaction when exposed to moisture such as Pop Rocks ® by General Foods Corporation. Inside circle opening 35, 35' can be a different soft, hard, and the like edible insert. Various formulas can be used to make the edible U-shaped members.

One type of gummy candy formula of ingredients followed by the Gelatin Manufacturers was Institute of America is shown in Table 1.

TABLE 1

| Part A | % | Part B | % | Part C | % |
| --- | --- | --- | --- | --- | --- |
| Water | 7.0 | Water | 14.5 | Water | 1.5 |
| Sugar corn | 30.0 | Gelatin | 7.8 | Citric Acid | 1.5 |
| Syrup | 35.4 | Sorbitol | 2.3 | Color/Flavor | Q.S. |

First, Part B of Table 1, is prepared by hydrating in cold water or dissolving in hot (170 F plus) water. The Sorbitol is added just prior to mixing the solution with gelatin. If hot water is used, the gelatin solution should be left undisturbed for approximately 10 to 15 minutes, when the surface foam is then skinned therefrom.

Part A of Table 1, is prepared by heating all the combined components at approximately 240 F, until approximately 86 to 87% solids appear and then add Part B. Then, the mixture should be agitated to minimize any incorporation of air, by using equipment such as a vacuum blender. Then, blend until the gelatin is fully dissolved and uniformly mixed. Finally, Part C is added, and the batch can be deposited into a mold within 30 minutes. After curing, the final pieces can be coated with a blend of 95% mineral oil, 2% carnauba wax, and 3% bee's wax.

Other formulas can be used for forming a combined Starch-Gelatin Gummy candy such as Formula No. AES 5154-178, by Staley Food Company, as shown in Table 2.

TABLE 2

| Ingredients | pounds | % dsd |
| --- | --- | --- |
| Part I. Main Slurry | | |
| Corn Syrup | 242 | 50.6 |
| Granulated Sugar | 150 | 38.3 |
| Starch | 26.5 | 6.1 |
| Water | 16 | — |
| Part II. Gelatin Solution | | |
| Gelatin | 22 | 5.0 |
| Water | 43.5 | — |

Using Table 2, Part I is mixed and heated as a main slurry to approximately 200–210 F. The Part II gelatin solution is premelted at approximately 160 F and added to the main slurry and mixed together. Next, the mixture is processed through a jet cooker at approximately 295 F. Color, flavor, and approximately 1.5% citric acid is then added. Approximately 78–79% solids is deposited into a 7% molding starch, where it is held at ambient temperatures, until it solidifies and then coatings such as oil are applied thereon.

FIG. 2 is a side view of two of the single teeth row member sets 1 and 1' of FIG. 1A together for use as both an upper teeth set 1 and as a bottom teeth set 1'.

Figure 3B:
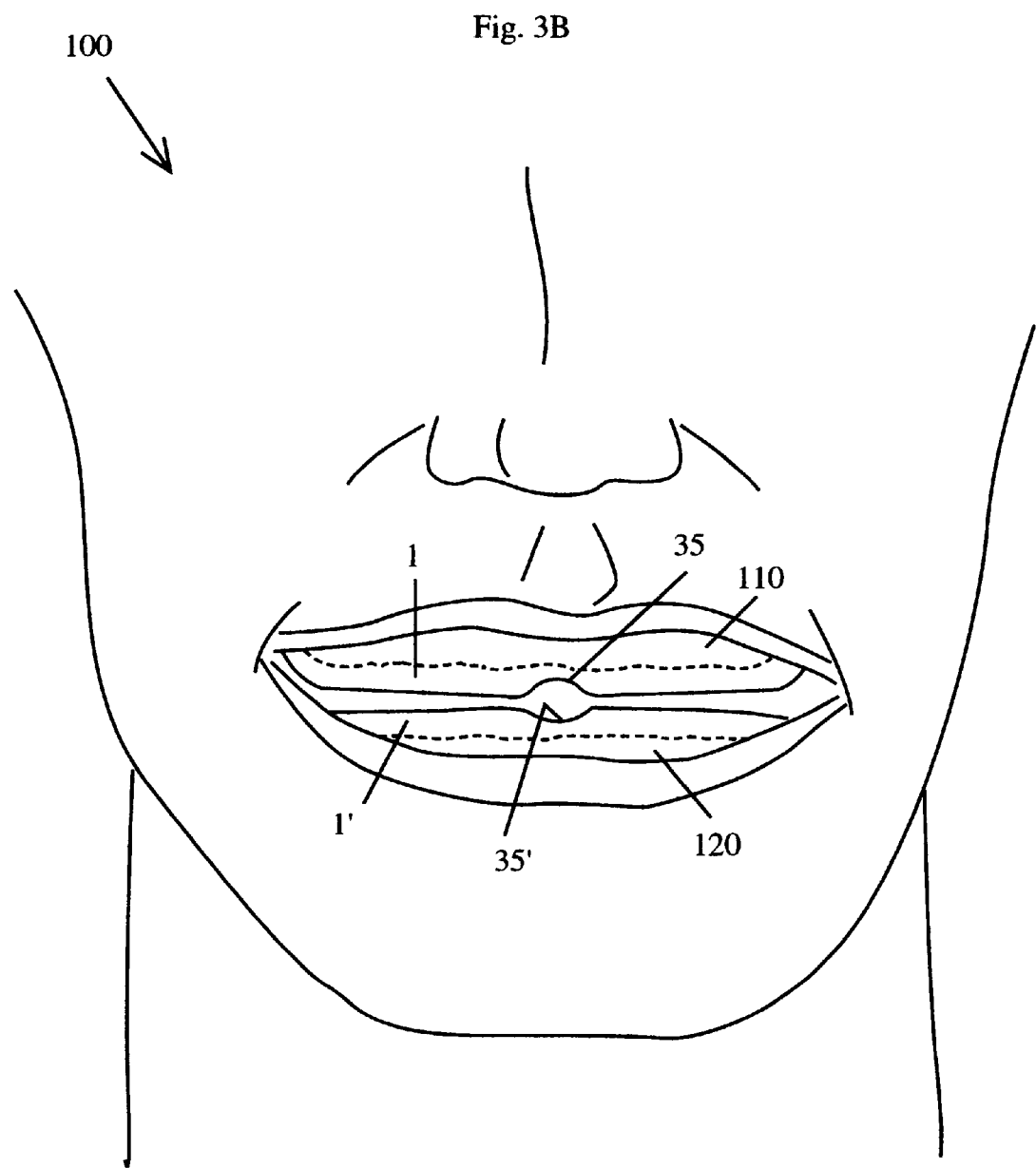
FIG. 3B is a front view of FIG. 3A along arrow E.
Figure 3C:
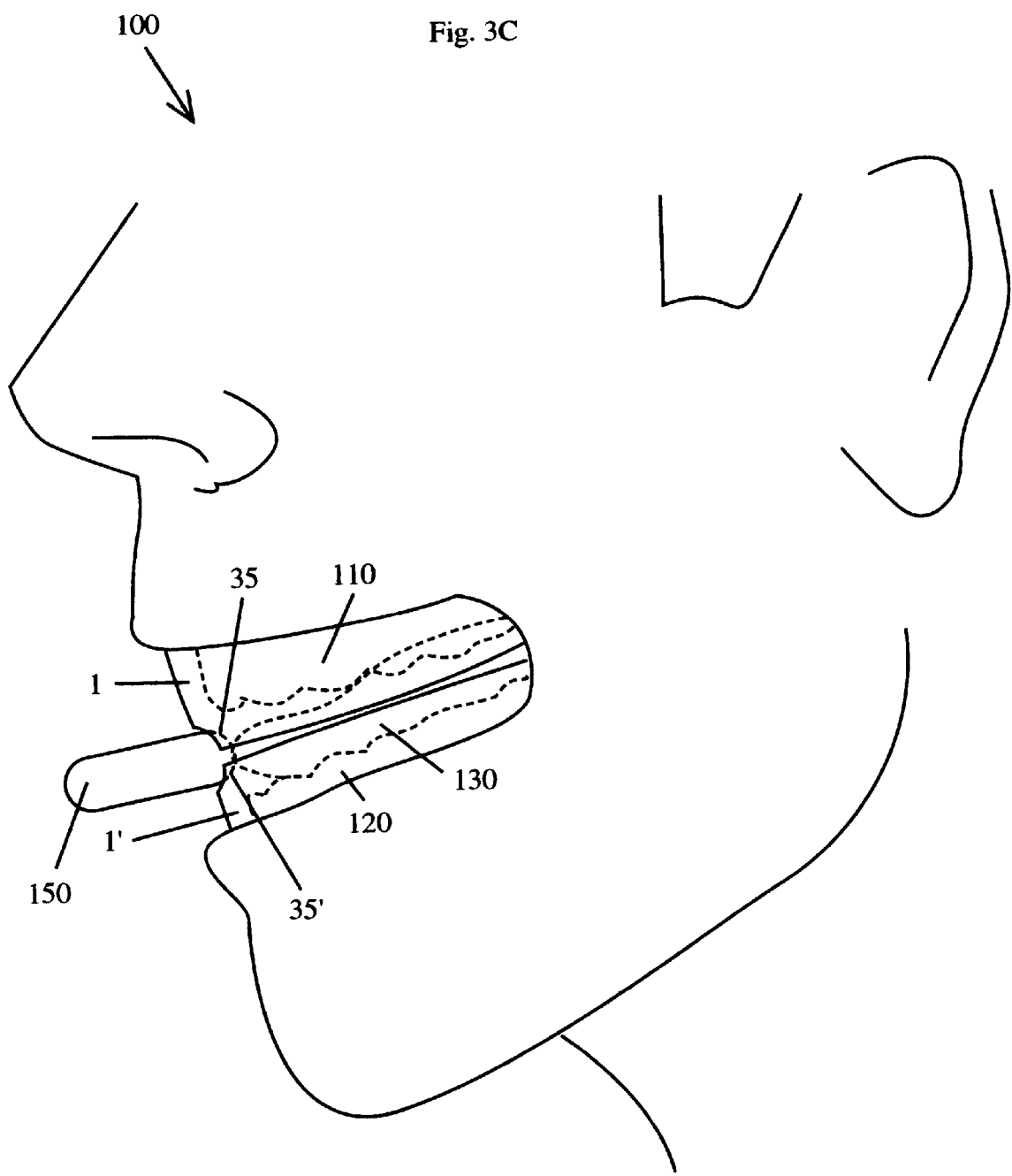
FIG. 3C is an enlarged side view of FIG. 3A showing the novel invention being applied.

FIG. 3A is a side view of a person 100 wearing two teeth member row sets 1 and 1' of FIG. 2 on their upper and lower teeth 110, 120, respectively, after the teeth have been clenched together and compressed into the pliable members 1 and 1'. FIG. 3B is a front view of FIG. 3A along arrow E, showing the upper semi-circle through-hole opening 35 of the upper set member 1, and the lower semi-circle through-hole opening 35' of the lower set member 1'. FIG. 3C is an enlarged side view of FIG. 3A showing the through hole formed by semi-circle openings 35 and 35' allowing a portion of another person's body part 150 such as a tip portion of a person's tongue, nipple, toes, fingers, clitoris, penis, and/or body fluids to pass therethrough, and contact the user's own internal mouth 130 such as the tongue, and the like.

FIG. 4A a second embodiment 200 perspective view of a single teeth row member set of the novel mouthpiece. FIG. 4B is a top view of the single teeth row member set 200 of FIG. 4A along arrow F. FIG. 4C is a bottom view of the single teeth row member set 200 of FIG. 4A along arrow G. FIG. 4D is a rear view of the single teeth row member 200 of FIG. 4A along arrow H. FIG. 4E is a front view of the single teeth row member 200 of FIG. 4A along arrow I. FIG.

4F is a rear view of the single teeth row member 200 of FIG. 4A along arrow H with semi-circle through-hole 35. FIG. 4G is a front view of the single teeth row member 200 of FIG. 4A along arrow I with semi-circle through-hole 35. FIG. 4H is a side cross-sectional view of a leg of the teeth row member 200 of FIG. 4B along arrow J.

Referring to FIGS. 4A–4H, embodiment 200 has a U-shaped configuration with two legs 210, 220 and center portion 230, similar to like corresponding components in the first embodiment, with the addition of having an interior U-shaped channel 215, 225, 235 inside. Each channel has a thickness t4 of approximately ¼ inch adjacent to the center portion 230, which tapers down to a thickness t3 of approximately ⅛ inch adjacent to leg ends 212, 222. The remaining detail is identical to that described in reference to the first embodiment 1.

FIG. 5 is a side cross-sectional view of the two single teeth members 200 and 200' of the preceding figures in position for being inserted into a wearer's mouth so that the wearer's teeth fit inside the channels. Leg ends 212, 222 can include walls similar to the channel sides so that the wearer clenching down on the pliable member indents the walls 212, 222.

Although the preferred embodiments have been described as using edible materials, the invention can be used with other materials such as but not limited to flavored silicone, flavored plastics, and the like, where the effect is also to provide a pliable flavored material that conforms to the upper and lower teeth of all consenting adults, and changes their sharp teeth edges into rounded soft surfaces, that can be used during oral sexual activities.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim:

1. An edible mouthpiece for oral sexual activities, comprising:
   a top edible member for fitting about an upper teeth portion of a user and being formed from a solid non-channeled material, the top edible member having a front thicker portion which tapers down to a thinner rear portion of the top edible member; and
   a bottom edible member for fitting about a bottom teeth portion of the user and being formed from a solid non-channeled material, the bottom edible member having a front thicker portion which tapers down to a thinner rear portion of the bottom edible member so that the top edible member and the bottom edible member can substantially and entirely abut against one another and form a complete mouth fit when the upper teeth portion and the bottom teeth portion are clenched together, wherein the top solid non-channeled material and the bottom solid non-channeled material allow for the top and the bottom portions of the teeth to compress into the top edible member and the bottom edible member and wherein the top edible member and the bottom edible member are utilized during oral sexual activities between consenting adults.

2. The edible mouthpiece of claim 1, wherein the top edible member and the bottom edible member are both formed from at least one material chosen from one of:
   a pliable jellied candy material, and a pliable gelatin candy material.

3. The edible mouthpiece of claim 1, wherein the top edible member and the bottom edible member are both formed from:
   a pliable licorice material.

4. The edible mouthpiece of claim 1, wherein the top edible member and the bottom edible member are formed from:
   a pliable chewing gum material.

5. The edible mouthpiece of claim 1, wherein the front portion has a thickness of approximately ½ inch which tapers down to the rear portion which has a thickness of approximately ¼ inch.

6. The edible mouthpiece of claim 1, wherein at least one of the top edible member and the bottom edible member includes:
   a through-hole adjacent to a center portion of the front of the teeth, for allowing at least one of a portion of a body part and a body fluid to pass there-through.

7. A two part pliable mouthpiece that is edible, comprising:
   a top pliable bridge member of edible material for conforming about an upper teeth portion of a mouth of a user which changes the upper teeth portion from hard and sharp to be soft and rounded, and being formed from a solid non-channeled material;
   a bottom pliable bridge member of edible material for conforming about a bottom teeth portion of the mouth of the user which changes the bottom teeth portion from hard and sharp to be soft and rounded, and being formed from a solid non-channeled material, wherein the top solid non-channeled material and the bottom solid non-channeled material allow for the top and the bottom portions of the teeth to compress therein; and
   a through-hole formed between the top and the bottom pliable bridge members adjacent to a center portion of the front of the teeth, for allowing at least one of a portion of a body part and a body fluid to pass there-through, wherein the top edible member and the bottom edible member allow for direct physical contact between the mouth of the user and another person.

8. The two part mouthpiece of claim 7, wherein both the top pliable bridge member and the bottom pliable bridge member have a front portion with a thickness of approximately ½ inch which continuously tapers down to a rear portion having a thickness of approximately ¼ inch, so that substantially all of a lower surface of the top pliable bridge member can substantially and completely abut against substantially all of an upper surface of the bottom pliable bridge member to allow a complete mouth fit when the top teeth portion and the bottom teeth portion are clenched together.

9. The two part mouthpiece of claim 7, wherein the top bridge member and the bottom bridge member are both flavored.

10. A two part pliable edible mouthpiece, comprising:
    a top edible pliable bridge member for conforming about an upper teeth portion of a mouth of a user which changes the upper teeth portion from hard and sharp to be soft and rounded, the top member having a front thick portion which continuously tapers down to a thin rear portion;
    a bottom edible pliable bridge member for conforming about a bottom teeth portion of the mouth of the user which changes the bottom teeth portion from hard and sharp to be soft and rounded, wherein the top edible member and the bottom edible member allow for direct physical contact between the mouth of the user and another person, the bottom member having a front thick portion which continuously tapers down to a thin rear portion so that substantially all of an upper surface of the bottom member can abut against substantially all of a lower surface of the top member to conform to a complete mouth fit when the top teeth portion and the bottom teeth portion are clenched together; and a through-hole formed between the top and the bottom pliable bridge members adjacent to a center portion of the front of the teeth, for allowing at least one of a portion of a body part and a body fluid to pass therethrough.

11. The two part pliable edible mouthpiece of claim 10, wherein the front portion has a thickness of approximately ½ inch which tapers down to the rear portion which has a thickness of approximately ¼ inch.

* * * * *